US006647293B2

(12) United States Patent
Meyer

(10) Patent No.: US 6,647,293 B2
(45) Date of Patent: Nov. 11, 2003

(54) METHOD FOR PREDICTIVELY CALCULATING A CARDIAC SIGNAL COURSE AND FOR CONTROLLING THE DELIVERY OF A STIMULATION PULSE BY AN IMPLANTABLE CARDIAC DEVICE

(75) Inventor: Wolfgang Meyer, Erlangen (DE)

(73) Assignee: Biotronik Mess-und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 0 days.

(21) Appl. No.: 09/764,343

(22) Filed: Jan. 19, 2001

(65) Prior Publication Data

US 2002/0087197 A1 Jul. 4, 2002

(30) Foreign Application Priority Data

Jan. 19, 2000 (DE) .......................... 100 01 890

(51) Int. Cl.$^7$ ................................ A61N 1/39
(52) U.S. Cl. ...................................... 607/5
(58) Field of Search .................. 600/509, 515, 600/518; 607/4, 5, 7, 11, 14

(56) References Cited

U.S. PATENT DOCUMENTS

| 5,020,540 A | 6/1991 | Chamoun |
| 5,211,179 A | 5/1993 | Haberl et al. |
| 5,921,940 A | * 7/1999 | Verrier et al. ............ 600/518 |
| 5,967,981 A | * 10/1999 | Watrous .................. 600/428 |
| 6,400,982 B2 | * 6/2002 | Sweeney et al. .......... 600/515 |

FOREIGN PATENT DOCUMENTS

| DE | 44 44 144 | 6/1996 |
| DE | 198 42 107 | 3/2000 |
| DE | 44 47 447 | 7/2000 |

OTHER PUBLICATIONS

Patent Abstracts of Japan , Publication No. 08098818, Publication Date apr. 16, 1996, "Diagnosis and Device Thereof", Kimura et al.

* cited by examiner

Primary Examiner—George R. Evanisko
(74) Attorney, Agent, or Firm—Browdy and Neimark, P.L.L.C.

(57) ABSTRACT

A method for the predictive calculation of a cardiac signal course incorporates the following process steps:
scanning of the time progression of a cardiac signal during a certain scanning period,
calculation of model coefficients according to the method of autoregressive modeling from the scanning values of the scanning period,
predictive calculation of anticipated signal values following the scanning period during a prediction period according to the method of autoregressive modeling based on the scanning values and model coefficients, with the signal values calculated iteratively, in each case by entering the last predicted signal value as the last scanning value during the autoregressive modeling.

5 Claims, 4 Drawing Sheets

METHOD FOR PREDICTIVELY CALCULATING A CARDIAC SIGNAL COURSE AND FOR CONTROLLING THE DELIVERY OF A STIMULATION PULSE BY AN IMPLANTABLE CARDIAC DEVICE

BACKGROUND OF THE INVENTION

1. Field of the Invention

The present invention pertains to a method for predictively calculating a cardiac signal course, and to a control method based thereon for the delivery of a stimulation pulse by an implantable cardiac device.

2. Background Art

Regarding the background of the invention, it needs to be explained that various pathological conditions of the heart are characterized by significantly propagating wave fronts of the electrical excitement of the myocardium. The occurrence of an atrial fibrillation (hereinafter: AF), for instance, is explained by tie propagation of wave fronts on the atrial myocardium. This wave propagation is reflected in the potential that is measured locally at a bipolar electrode.

In accordance with relevant medical findings, it is known to apply a stimulation pulse with the aid of an electrode during the so-called "excitable gap"—i.e., the short period before a new wave front characterizing a fibrillation condition arrives at the location of the electrode and after the local refraction time has elapsed—which effects a sort of "reset" for the entire cardiac muscle apparatus and stops the fibrillation. This method must be distinguished from conventional defibrillation methods, however, which can react only to the arrival of the wave front, because it requires less defibrillation energy and prevents side effects, such as the triggering of ventricular tachycardia or of a post-defibrillatory bradycardia.

Various approaches for the treatment of tachycardic conditions of the heart have already become known from the prior amt. EP 0 830 876 A1, for instance, deals with an implantable device for early detection and suppression of tachycardia in the heart in which a microelectrode away that is in contact with the cardiac muscle tissue detects the stimulus conduction potentials in the cardiac muscle tissue. A measuring device determines the refractory time of the cardiac muscle cells in the monitored cardiac region and the stimulus conduction velocity in the monitored cardiac muscle region. The product value of the refractory time and stimulus conduction velocity is representative for the tachycardia risk. If the product value falls short of a certain tachycardia threshold value, this signals a condition of the heart in risk of tachycardia. If such a condition has been detected, an anti-tachycardia stimulation pulse may be delivered with the aid of a stimulation arrangement.

This prior art has the shortcoming that, due to the microelectrode array that needs to be provided, the implantable cardiac device revealed there cannot be implemented simply by equipping a pacemaker or defibrillator with otherwise customary external characteristics with die corresponding control technology.

SUMMARY OF THE INVENTION

In order to be able to work with a conventional implant design, ways must be found whereby the excitable gap in the atrium is determinable and whereby the local potential curve at the location of the electrode is predictable. In this context, it needs to be noted that the entire spatial and temporal distribution of the local potentials over the atrium, or information on the inner degrees of freedom of the myocardium cells, are not available.

As an approach to solving the above problems the present invention now proposes a method for the predictive calculation of a cardiac signal course, the essential process steps of which are scanning of the time progression of a cardiac signal during a certain scanning period, calculation of model coefficients according to the method of autoregressive modeling from the scanning values of the scanning period, predictive calculation of anticipated signal values following the scanning period during a prediction period according to the method of autoregressive modeling based on the scanning values and model coefficients, with the signal values calculated iteratively, in each case by entering the last predicted signal value as the last scanning value during the autoregressive modeling.

In this approach, the invention is based on the realization that the atrial fibrillation, as an example for a pathological condition of the heart, represents an irregular process, which appears at a local electrode as they are used in pacemakers or defibrillators, partly as an irregular potential course, partly in the form of organized potential structures. These observed irregularities raise the question whether an atrial fibrillation must be considered chaotic due to the numerous non-linearities in biological systems, and whether corresponding analysis and control methods should, therefore, be used. However, up to now, the occurrence of chaotic conditions in fibrillation episodes has not been proven. On the contrary, preliminary tests during the development of the method according to the present application, for example with the aid of the non-linear approximation of measured signals and determination of the so-called Lyapunov exponents, and also a qualitative study of measured signals, have not revealed any compelling insights indicating the presence of a deterministic exponential divergence of the fibrillation potentials. Specifically, frequent transitions between periodic segment and irregular intervals can be detected during acute atrial fibrillation. This is an indication that both a strong linear component, as well as stochastic influences are present in the case of an AF potential course and propagation. Even though the future identification of chaotic contributions, which could then be calculated predictively according to the invention with a non-linear autoregressive model, to the atrial fibrillation cannot be ruled out in this context, based on the current state of the scientific research it is not possible to derive any method for predicting the potential curve during atrial fibrillation and/or for a therapeutically effective control of implantable cardiac devices in the sense of an active termination of the fibrillation condition from die speculation concerning chaotic behavior. However, this qualification does not apply for the prediction of the fibrillation initialization with the aid of the essentially autonomously determined sequences prior to the actual occurrence of an atrial fibrillation.

In this sense, a cardiac signal such as, e.g., an EKG signal, is scanned during a certain scanning period, and the appropriate measuring points are recorded. Model coefficients are calculated from the scanning values of the scanning period according to the method of autoregressive modeling, and anticipated signal values following a scanning period are, in turn, precalculated according to the method of autoregressive modeling during a certain prediction period based on the scanning values ad model coefficients. These signal values now indicate, for example, the approach of an excitation front toward the scanning electrode so that an anti-tachycardia pulse can be delivered by the implant at a physiologically meaningful moment prior to the calculated arrival of the wave front Compared to other conceivable mathematical methods, the linear autoregressive prediction represents the most promising approach for the precalculation of the atrial potential course, since the concept essentially is very simple and takes into account especially periodic linear components, which dominate in AF potentials.

Preferred method characteristics, the content and meaning of which will be explained in more detail below based on an embodiment presented by way of example.

Further preferred embodiments of the invention pertain to a method for controlling the delivery of a stimulation pulse by an implantable cardiac device, whereby an abnormal cardiac signal value curve can be calculated in advance with the aid of the prediction method of the basic invention, and whereby a stimulation pulse counteracting same is to be delivered accordingly within the prediction period. Specifically, the implantable device is controlled such that for an atrial fibrillation the stimulation pulse is applied in the excitable gap prior to the arrival of a precalculated wave front at the excitation electrode that delivers the pulse A further preferred embodiment of the invention pertains to the implantable cardiac device as such, which, in addition to the commonly present control unit, measuring electrode and stimulation electrode, incorporates a computing device for the predictive calculation of a cardiac signal course according to the invention, and a stimulation unit, which can be operated with the control method according to the invention, for the electrical actuation of the stimulation electrode.

BRIEF DESCRIPTION OF THE DRAWING

The invention will now be explained in greater detail below, based on the appended drawings, in which.

DESCRIPTION OF THE PREFERRED EMBODIMENT

Figure 1A:
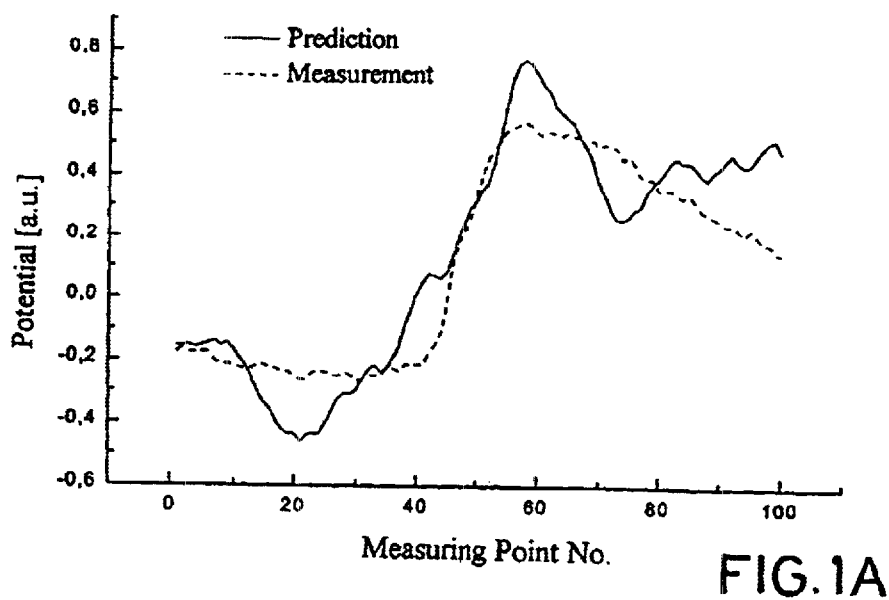
FIG. 1A shows a curve diagram of the time progression of the precalculated signal course and the actual measured signal of a cardiac potential.

As an introductory remark, it needs to be explained that the measuring results on which the following description is based, are based on potential signals that were derived via a bipolar MAP electrode placed in the epicardium of a patient after an aortic valve replacement. In future practice, shown in FIG. 1B an implantable cardiac device 10, such as a pacemaker or defibrillator, may have a microprocessor-based control unit 20 of the usual design that performs the customary device-internal control processes, the processing of any data and signals fed to the implant from outside, and particularly also the calculation processes for the predictive calculation of the potential in the atrial myocardium that represents the propagating AF wave front. A measuring electrode 30, which may be formed separate from, or in one unit with a stimulation electrode 40, is provided for scanning the potential curve. This stimulation electrode may be electrically actuated by a stimulation unit 50 in the implantable device in order to deliver an appropriate stimulation pulse to the heart which is applied based on the precalculated signal curve in the excitable gap prior to the arrival of the precalculated wave front.

Before discussing the actual method for the predictive calculation of a cardiac signal curve, the method of autoregressive modeling, on which this invention is based, shall be briefly illustrated as explained by W. H. Press et al. in the technical article "Numerical Recipes in C", University Press, Cambridge 1992.

Accordingly, the basic equation of the autoregressive modeling is as follows:

$$y(n) = \sum_{j=1}^{M} d(j)y(n-j) + x(n)$$

It means that a future measuring value y(n) that is to be precalculated is modeled at the scanning time n of a signal as a linear combination of the M preceding values in such a way that M model coefficients d(j) occur with j=1 ... M, and a prediction error x(n) is accepted. The model coefficients are determined by determining the mean square prediction error over N>=M measuring points. Once the coefficients have been determined, the next value can be precalculated in each case with the aid of the basic equation.

The expansion to the prediction of a larger number of unknown measuring points, i.e., especially the predictive calculation of anticipated signal values following the actual scanning period during a prediction period on the basis of the scanning values takes place by entering the first precalculated value as the last actual measured value into the above equation and repeating the precalculation for this new set of data. The signal values are thus calculated iteratively by entering, in each case, the last precalculated signal value as the last scanning value during the autoregressive modeling.

In principle, the coefficients can be determined anew for each prediction step with a constant measurement window—ie., the M preceding values—however, this is not done in the studies and calculations on which the embodiment is based. Instead, a new set of model coefficients is determined only when signal values are precalculated in a new prediction period, i.e., the calculation of the coefficients takes place anew only when the window of known measured data used for the prediction is shifted.

The following examples were performed with different values for the parameter M, i.e., different orders of the autoregressive model. Below, model orders or model windows of M=10000 will be used initially.

First the coefficients d(j) are determined with the aid of the standard method according to Press et al. (in the referenced work). This is essentially done with the following steps:

In the prediction of the scanning value y(n) at the location n with the aid of an autoregressive model, a deviation x(n)

of the prediction from the actual measured value usually occurs:

$$y(n) = \sum_{j=1}^{M} d(j)y(n-j) + x(n).$$

The coefficients d(j) are, therefore, determined such that the mean square deviation $$<x(n)^2>$$

becomes minimal for predictions within the known data set of the length N that serves as the basis for the prediction. With the known autocorrelation function Φ(j) of the known scanning values $$\Phi(j) \cong (N-j)^{-1} \sum_{i=1}^{N-j} y(i)y(i+j),$$

the demand for the minimization of the prediction error x(n) results in a system of M linear equations for the desired values d(j):

$$\sum_{j=1}^{M} \Phi(|j-k|)d(j) = \Phi(k).$$

Solving this system for d(j) and, hence, the determination of the parameters of the autoregressive model, takes place by triangulation of the coefficient matrix associated with the linear equation system, e.g., with the aid of the method of elimination according to Gauss-Jordan.

Furthermore, the length of the signal curve to be predicted must be established as a further parameter. In the following sample calculations it is kept constant at p=100. The calculations are then made in each case based on a window containing the number of measuring points N=M+1. After the predictive precalculation of 100 measuring points with fixed model coefficients the window is shifted by one point. Afterwards the model coefficients are again adjusted and calculated, and a new predictive calculation is performed.

Translated into practical measurement parameters this means that at a scanning rate of the excitation potential of the heart of 500 Hz, the length p=100 of the signal to be precalculated represents a prediction period of 200 ms. The model order or measurement window of the length=10000, accordingly, corresponds to a scanning period of 20 s. If the measurement window is shifted in 5000 steps, the predictive calculation is performed from scanning values in the form of data measured over 20 seconds into a prediction period of 200 ms in the future, and the entire precalculation is performed for a period of 10 seconds of each scanning step.

Figure 1B:
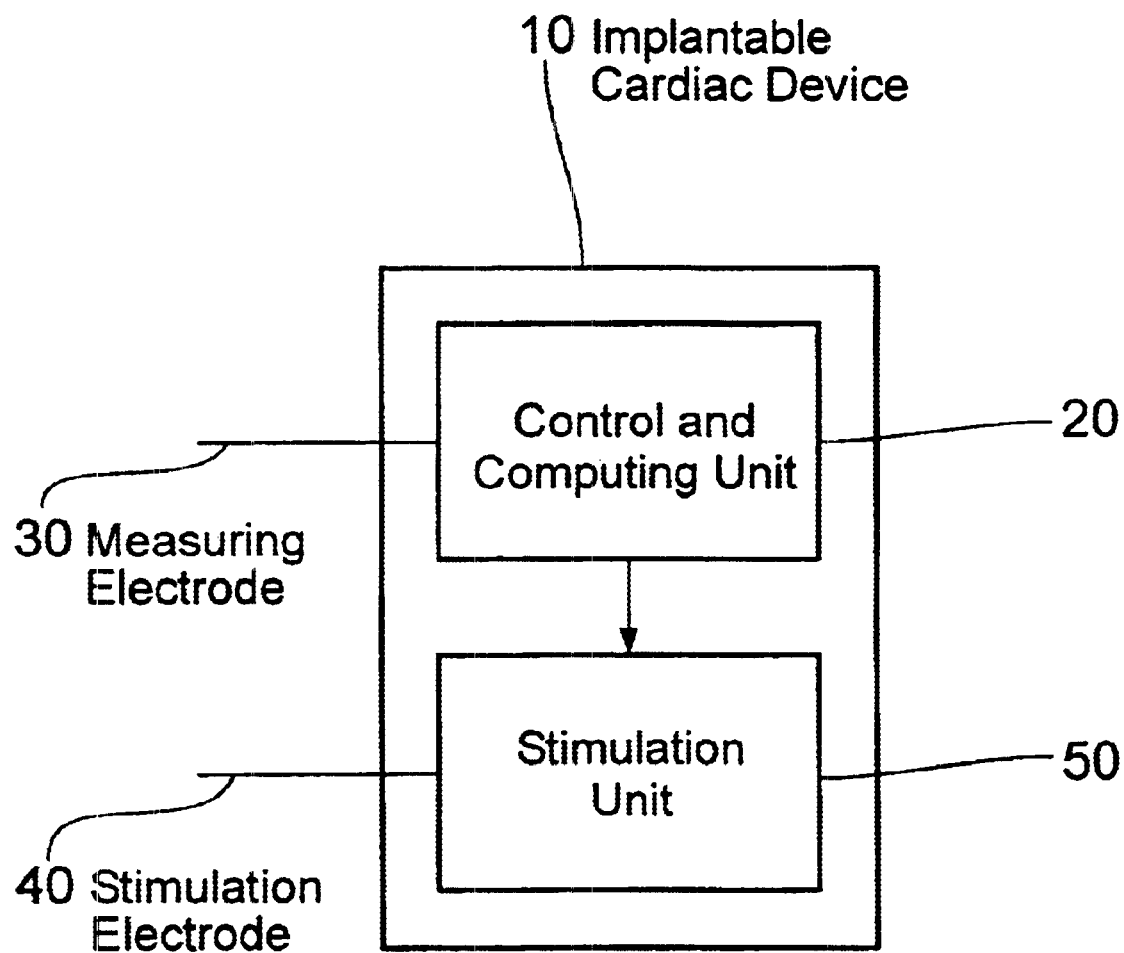
FIG. 1B shows an implantable device of the present invention.

If this is done based on a practical measurement this produces the anticipated signal values that have been entered in FIG. 1A with a continuous line. FIG. 1 shows a typical curve of the predictively precalculated signal in a window of a length of 200 ms with M=10000.

For control purposes, the above explained measuring set-up was also used to record the actual curve of the potential signal for the measurement window. This produces the curve shown in FIG. 1A with a dashed line. While it is true that it differs in certain details when compared with the precalculated curve (continuous line), a global congruence between main criteria, such as the positions of the rise and maximum of the potential signal, can be noted with a high level of significance.

If the anticipated signal curve is now continually precalculated in the described manner with the inventive method in an implantable cardiac device based on the measured data available there, and a signal curve according to FIG. 1A is obtained for a certain prediction period, the implantable device "knows" that it is highly probable that an AF wave front is headed towards its measuring electrode. Since it precalculates this abnormal cardiac signal value course, a stimulation pulse that counteracts this abnormal signal course, and thus the propagating wave front, can be delivered to the heart within the prediction period in the so-called "excitable gap", so that the wave front is interrupted and a fibrillation can be terminated.

In order to now evaluate the quality of the above-explained precalculation method, a total of 5000 precalculations and their correlation with the measured signal curve were used as a basis, based on 5000 shifts of the measurement window. Statistical parameters for the distribution of the correlation, which are shown in the following table, were determined for 5000 precalculations over 200 ms using customary statistical analysis methods:

|  | M = 1000 | M = 5000 | M = 10000 |
| --- | --- | --- | --- |
| Mean value | 0.52 | 0.56 | 0.59 |
| Standard Deviation | 0.36 | 0.29 | 0.28 |
| Skewness | 6.00 | 4.69 | 4.79 |
| Median | 0.62 | 0.62 | 0.66 |

Figure 2:
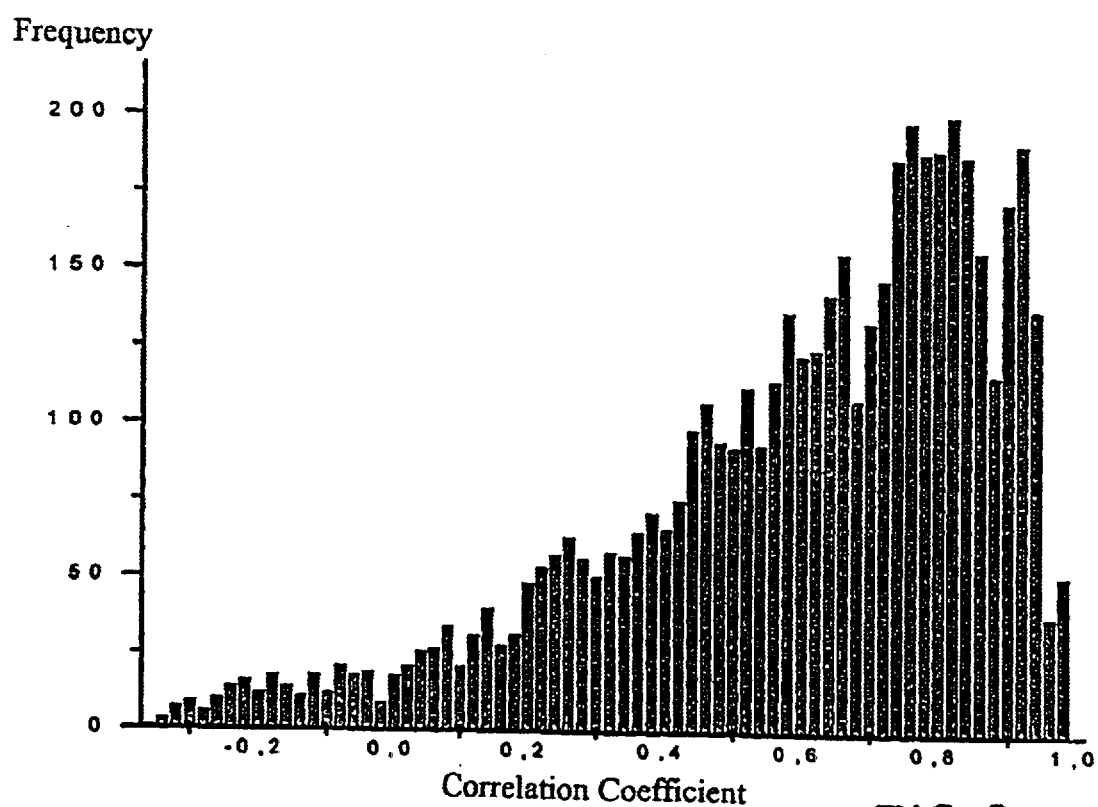
FIGS. 2 and 3 show histograms of the linear correlation coefficient between the precalculated signal course and the measured signal for different orders of the autoregressive model function.
Figure 3:
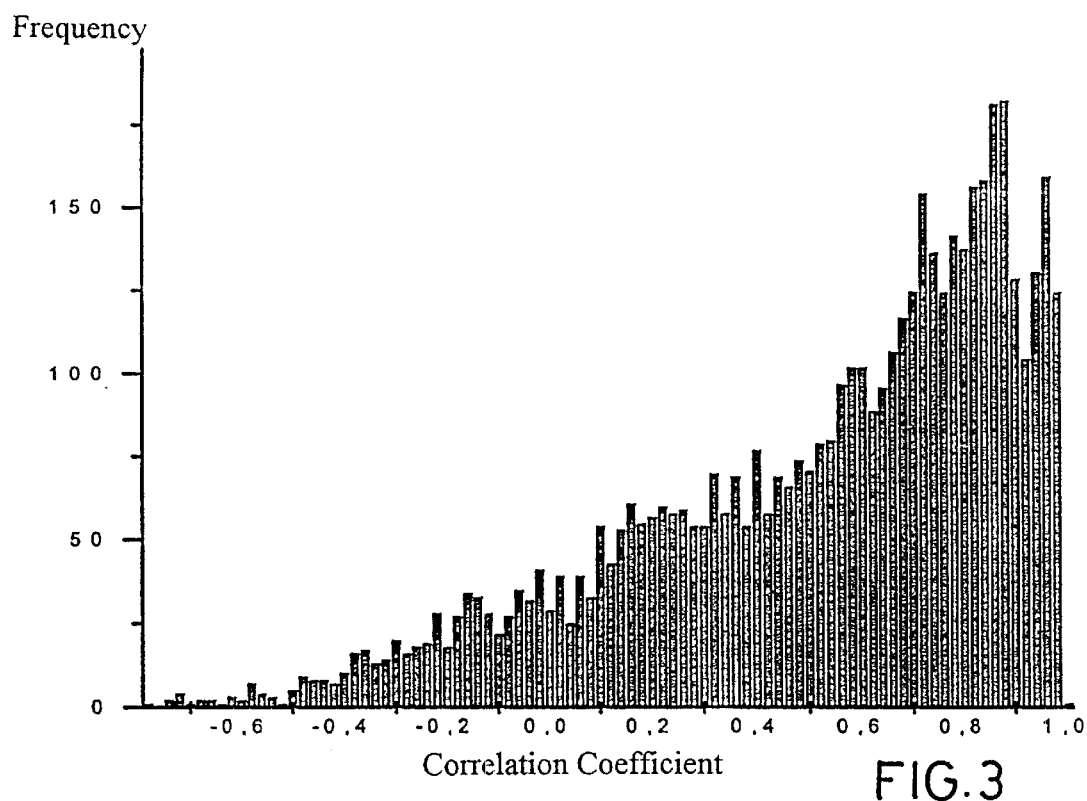

The corresponding histograms are shown in FIGS. 2 and 3 for M=10000 (FIG. 2) and M=1000 (FIG. 3).

In summary, the table and the two histograms show the following with regard to statistics: the mean value increases with the order of the model. The median is the highest at M=10000, which corresponds to a maximum number of high positive correlations. All distributions have a high measure of skewness, which does not correlate with the order M. Since the predictability can furthermore be considered the better the fewer coefficients occur in the range of the zero or in the negative range, the prediction is qualitatively best at M=10000. In fact, as it becomes apparent from FIG. 2

The negative correlations can be attributed to transitions in the signal course, e.g., between irregular and largely periodical behavior. The fact that the absolute number of negative correlations is distinctly different from zero is due to the use of a shifting window.

Besides the correlation between the actual courses of the precalculated signal and the actual measured signal, the correct prediction of the "upstroke" of the maximum is also of importance within the framework of the present invention, which will be examined below for the previously used order M=10000 of the autoregressive model. This is done by examining, according to the following algorithm, how near the prediction of an increase in potential corresponding to an approaching wave font comes to the actual increase and thus to the arrival of the wave front. First the maximum of the precalculated signal course is searched. If it is located in the left half of the prediction period, the precalculation is disregarded, since the wave front has likely already arrived, and/or an effective cancellation by applying a counter-stimulation pulse is no longer possible. If the maximum lies in the right half of the prediction period, the mean values of the prediction and actual measured signal are determined. The point in time at which the precalculated signal course and the actual measured value pass through their mean values is defined as the beginning of the "upstroke". The corresponding points in time can now be compared and a statistic of their discrepancies can be prepared.

Figure 4:
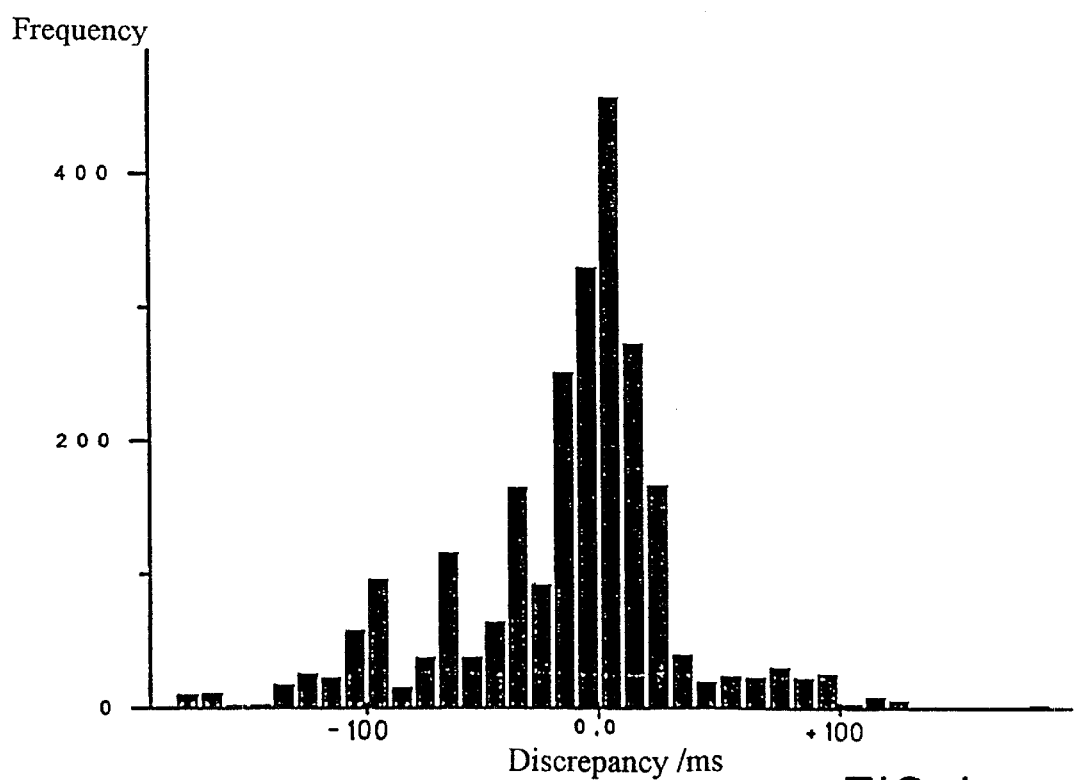
FIG. 4 shows a diagram for the distribution function of the discrepancies between the precalculated signal curve and the measured signal.

The result of this study is shown in FIG. 4. It shows that the distribution function has relatively wide extensions around a distinct maximum around the discrepancy 0.0, which can be attributed, among others, to the definition of the "upstroke". Since a high concentration of the distribution values is present around the discrepancy 0.0, the time of the upstroke can be precalculated within a narrow range with the aid of the simple method of the autoregressive modeling. A quantitative analysis reveals that approximately 36% of all predictions yield a discrepancy with an absolute value<10 ms and thus lie within a window of the width of 20 ms around the actual "upstroke".

If one now assumes that the "excitable gap" has a width of exactly 20 ms, and that the offset between the effective stimulation and the beginning of the wave front, as well as the width of the "upstroke," can be estimated and are largely constant, the likelihood according to this approach that the "excitable gap" will be encountered when an extra stimulus is applied amounts to a multiple of the likelihood for an uncoordinated stimulation. In fact, in the latter situation, the likelihood that a single stimulus will find the excitable gap is equal to the ratio of the ties in which the tissue is excitable and those in which it is not excitable.

Since, for the practical application of the inventive method in implantable cardiac devices, the number of required calculations is to be as low as possible due to the limited capacity of such devices—which is not the case with a model order of M=10000—the inventive prediction method was analyzed also with respect to lower model orders. The scanning rate was reduced from 500 Hz to 50 Hz. In this way the same time scale as in the above-discussed analyses is already attained at 10 instead of 100 precalculated signal values. At the same time the temporal resolution for the location of the precalculated "upstroke" decreases and is also 10 ms. The model order is reduced to M=1000.

Figure 5:
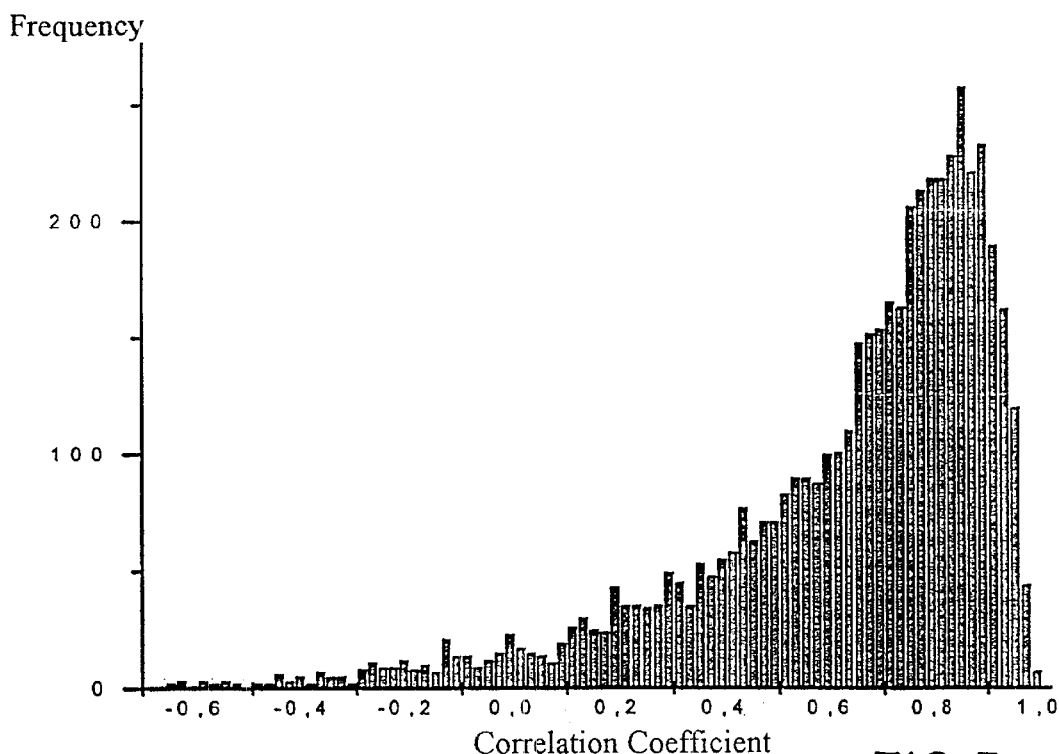
FIG. 5 shows a histogram of the correlation between the precalculated signal curve and the measured signal at a reduced scanning rate.

The histogram according to FIG. 5 and the following table provide corresponding calculations for statistical parameters.

|  | M = 10000 (500 Hz) | M = 1000 (50 Hz) |
| --- | --- | --- |
| Mean value | 0.59 | 0.63 |
| Standard deviation | 0.28 | 0.29 |
| Skewness | 4.79 | 5.63 |
| Median | 0.66 | 0.72 |
| Percentage in the area of ± 10 ms around the actual "upstroke" | 36% | 32% |

Figure 6:
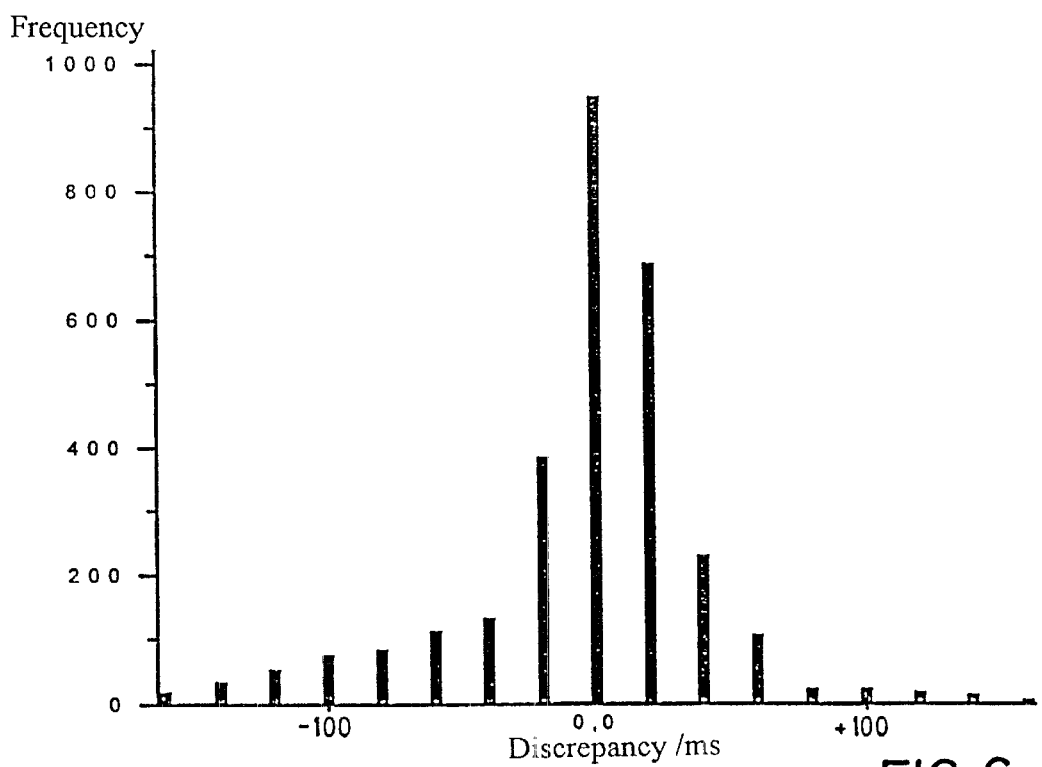
FIG. 6 shows a diagram for the distribution function of the discrepancies between the precalculated signal curve and the measured signal at the scanning rate according to FIG. 5.

From this results that, qualitatively, the correlation at a reduced scanning rate largely conforms to the results at a scanning rate of 500 Hz. Only one extension of the distribution is extended to stronger negative correlations. Furthermore, at 32%, the ratio of the precalculations for the "upstroke" that fall around the actual "upstroke" within an interval of a width of 20 ms lies only slightly below tile ratio of 36% at a scanning rate of 500 Hz. The quality of the precalculations has thus deteriorated only slightly due to the reduced scanning rate, which is also evident from the distribution function of the discrepancies according to FIG. 6. It differs from the diagram according to FIG. 4 only in the reduced resolution of only 20 ms. Discrepancies that lie between +/−10 ms are thus assigned to the discrepancy 0.0 ms.

In summary, both the distributions with a scanning rate of 500 Hz, as well as those on the basis of the reduced scanning rate of 50 Hz, differ significantly for correlations and discrepancies from the corresponding distributions in a purely stochastic system. If the precalculated global signal curve in the prediction period were not correlated with the actual signal curve, the corresponding distributions would be arranged as symmetrical Gauss curves around the correlation coefficient r=0.0. Furthermore, if there were no correlation between the predicted "upstroke" and the actual increase of the maximum rise, the distribution of the discrepancies would be flat. To this extent the discussed statistical analyses clearly show the functionality and practical capability of the inventive method.

What is claimed is:

1. A method for controlling the delivery of a stimulation pulse by an implantable cardiac device, comprising the following process steps:

scanning a cardiac signal during a scanning period;

providing scanning values derived during said scanning step;

calculating model coefficients according to a method of autoregressive modeling from the scanning values derived during said scanning step;

precalculating, during a prediction period, anticipated signal values following the scanning period according to the method of autoregressive modeling based on the scanning values and the calculated model coefficients;

iteratively calculating the anticipated signal values by entering a last anticipated signal value as a last scanning value in the method of autoregressive modeling; and when said step of precalculating produces an abnormal signal value, applying a stimulation pulse that counteracts the abnormal signal value at a point in time determined from said step of precalculating, wherein said step of precalculating is performed to precalculate the propagation of wave fronts on the atrial myocardium of the heart and to determine the time of an excitable gap prior to the arrival of a precalculated wave front at a stimulation electrode of the implantable cardiac device, and said step of a stimulation pulse is carried out, when the abnormal signal value indicates an atrial fibrillation, to apply the stimulation pulse in the excitable gap.

2. The method of claim 1, wherein said step of scanning is carried out by scanning an excitation potential of the heart during a propagation of wave fronts if the excitation potential on an atrial myocardium.

3. The method of claim 2, wherein said step of scanning is carried out with a bipolar electrode.

4. The method of claim 1, wherein the method of autoregressive modeling according to which said step of calculating model coefficients is performed is an autoregressive linear modeling method.

5. An implantable cardiac device comprising:

a control unit;

a measuring electrode for scanning a cardiac signal during a scanning period;

a computing device for predictively calculating a cardiac signal curve, said computing device comprising:

means for providing scanning values derived during scanning by the measuring electrode;

means for calculating model coefficients according to a method of autoregressive modeling from the scanning values derived during the scanning period;

means for precalculating, during a prediction period, anticipated signal values following the scanning period according to the method of autoregressive modeling based on the scanning values and the calculated model coefficients; and means for iteratively calculating the anticipated signal values by entering a last anticipated signal value as a last scanning value in the method of autoregressive modeling;

a stimulation electrode; and a stimulation unit, which, when said means for precalculating produces an abnormal signal value, causes said stimulation electrode to apply a stimulation pulse that counteracts the abnormal signal value at a point in time determined from the precalculation performed by said means for precalculating wherein said means for precalculating anticipated signal values precalculate the propagation of wave fronts on the atrial myocardium of the heart and determines the time of an excitable gap prior to the arrival of precalculated wave front at the stimulation electrode of the implantable cardiac device, and wherein said stimulation unit is controlled, when the abnormal signal value indicates an atrial fibrillation, to apply the stimulation pulse in the excitable gap.

* * * * *